United States Patent [19]

Amelse et al.

[11] Patent Number: 5,030,788

[45] Date of Patent: Jul. 9, 1991

[54] CATALYZED XYLENE ISOMERIZATION UNDER SUPERCRITICAL TEMPERATURE AND PRESSURE CONDITIONS

[75] Inventors: Jeffrey A. Amelse, Batavia; Nancy A. Kutz, Wheaton, both of Ill.

[73] Assignee: Amoco Corporation, Chicago, Ill.

[21] Appl. No.: 410,664

[22] Filed: Sep. 21, 1989

[51] Int. Cl.$^5$ .............................................. C07C 5/22
[52] U.S. Cl. .................................. 585/480; 585/477; 585/481
[58] Field of Search ....................... 585/477, 480, 481

Primary Examiner—Curtis R. Davis
Attorney, Agent, or Firm—Reed F. Riley; Reed F. Riley; William H. Magidson

[57] ABSTRACT

A catalyzed process for the isomerization of a xylene-containing stream containing a major amount of ethylbenzene under supercritical temperature and pressure which contacts the stream under supercritical conditions with a catalyst and subsequently reduces the temperature of the isomerization product at a pressure above the critical pressure.

8 Claims, 3 Drawing Sheets

CATALYZED XYLENE ISOMERIZATION UNDER SUPERCRITICAL TEMPERATURE AND PRESSURE CONDITIONS

BACKGROUND OF THE INVENTION

This invention relates to a supercritical conditions, gas phase process for catalytically isomerizing a xylenecontaining stream to a product rich in p-xylene (pX) and thereafter reducing the temperature of said product such that it passes directly from said gas phase to a liquid phase without a phase change, and, more particularly, to a supercritical conditions, gas phase process in which both temperature and pressure are above their critical values, to isomerize a xylene-containing stream, optionally containing a minor amount of ethylbenzene (EB), to a product rich in p-xylene over a catalyst, and thereafter reducing the temperature of the product such that it passes directly from said gas phase to the liquid phase without a phase change.

Typically, p-xylene is derived from mixtures of $C_8$ aromatics separated from such raw materials as petroleum naphthas, particularly reformates, usually by isomerization followed by, for example, lower-temperature crystallization of the p-xylene with recycle of the crystallizer liquid phase to the isomerizer. Principal raw materials are catalytically reformed naphthas and petroleum distillates. The fractions from these sources that contain the $C_8$ aromatics vary quite widely in composition but will usually contain 10 to 35 weight percent ethylbenzene and up to about 10 weight percent primarily $C_9$ paraffins and naphthenes with the remainder being primarily xylenes divided approximately 50 weight percent meta, and 25 percent each of the ortho and para isomers. Feeds that do not have the primarily $C_9$ paraffins and naphthenes removed by extraction are termed "unextracted" xylene feeds.

The xylene isomerization process is an important step in the eventual production of polyester based upon terephthalic acid. The p-xylene isomerization product is oxidized to terephthalic acid, conveniently by a cobalt ion/acetic acid, liquid-phase oxidation, and serves as a raw material for the production of polyethylene terephthalate.

Xylene isomerization is performed commercially in the vapor phase or the gas phase at pressures well below the critical pressure of the xylene stream using a catalyst that exhibits catalytic activity for both the isomerization of xylenes and the conversion of at least a portion of the ethylbenzene impurity present in the feedstock. Isomerization in the liquid phase is preferred, but a number of problems, including low catalyst activity at temperatures required to maintain reactor contents in the liquid phase, are encountered. In a supercritical conditions xylene isomerization process, higher temperatures would be used so the problem of low catalyst activity associated with liquid phase operation is reduced.

It is common practice to add substantial amounts of hydrogen during vapor phase or gas phase xylene isomerization, as currently practiced, in order to slow catalyst deactivation. Hydrogen-to-hydrocarbon mol ratios are typically in the range from about 2 to about 10. The operation of a recycle gas compressor to supply such amounts of hydrogen can represent a substantial expense, and elimination of the recycle gas compressor has been cited as an incentive for liquid phase isomerization. It has been discovered that by proper choice of catalyst, acceptable catalyst life can be obtained during xylene isomerization at supercritical conditions without the addition of hydrogen and the recycle gas compressor eliminated in supercritical conditions isomerization as well.

Compared to current processes, a supercritical conditions xylene isomerization process also can offer substantial reduction in fuel for the furnace that is used to increase the temperature of the reactor feed to the desired reactor temperature. This reduction is due to higher average heat transfer coefficients for supercritical fluids.

In current processes a temperature pinch point occurs in the feed-effluent heat exchangers used to preheat the reactor feed and cool the reactor effluent at a point internal to the heat exchanger, i.e., not at either the hot or cold end. Temperature approach is defined as the difference in temperature between the heated and cooled streams at a point within the heat exchanger. A temperature pinch point is defined as a point where there is a minimum in temperature approach. The minimum in currently used processes can be substantially below the temperature difference between the hot and cold streams at other points within the heat exchanger, and in particular, substantially below the temperature difference at the hot end of the heat exchanger.

Since the rate of heat transfer is generally proportional to temperature approach, it is desirable to maximize temperature approach at points within the heat exchanger. However, the temperature approach at the hot end of the heat exchanger, where the reactor effluent enters the exchanger and the feed stream exists, is essentially proportional to fuel consumption in the furnace ahead of the reactor. Thus, it is desirable to minimize temperature approach at the hot end of the feed-effluent heat exchanger. The low average heat transfer coefficients and the temperature pinch point limit the temperature approach at the hot end of the feed-effluent heat exchanger that can be achieved economically for existing vapor or subcritical gas phase processes. The temperature approach at the hot end of the feed-effluent heat exchanger is in the neighborhood of 80°-120° F. for currently practiced processes. This means that for current isomerization processes the temperature of the feed stream to the reactor must be increased by an additional 80°-120° F. by passing the stream through a furnace, for example, after it leaves the feed-effluent heat exchanger. The heat required to effect the temperature increase represents a cost associated with the process. The desire to lower temperature approach at the hot end of the feed-effluent heat exchanger is balanced by the fact that lowering the temperature approach at the hot end of the feed-effluent heat exchanger requires increasing the surface area of the exchanger, which also increases capital costs. By operating above the critical pressure, it is possible to substantially reduce the magnitude of the temperature pinch or to move the point of lowest temperature approach to the hot end of the feed-effluent heat exchanger. Together with the higher average heat transfer coefficients, this will allow a lower temperature approach at the hot end of the feed-effluent heat exchanger for given heat exchanger surface area, and therefore, reduce fuel consumption.

Isomerization of xylenes in the liquid phase has been a subject of study by a number of workers. See for example, U.S. Pat. Nos. 3,777,400; 3,856,871; 4,268,420; and 4,269,813; Japanese Kokai 57-32233 (1982); and a 1972 article in "Hydrocarbon Processing" at p. 85 by P.

Grandio, F. H. Schneider, A. B. Schwartz and J. J. Wise. In these reports, the primary reaction observed was isomerization of xylenes, even in the presence of ethylbenzene and other impurities. Most of the catalysts which were employed in the above works contained zeolites of the large-pore type, e.g., faujasite-type zeolites or mordenite.

U.S. Pat. No. 3,856,879 is an early report of the use of shape-selective, molecular-sieve-containing catalysts for the isomerization of xylenes and the conversion of ethylbenzene in the liquid phase. The aluminosilicate zeolites ZSM-5, ZSM-12, and ZSM-21 are recommended for use in this process. Although by-product distributions are not reported in the patent, the xylene feed is said to be isomerized to its equilibrium isomer concentrations and the ethylbenzene converted via the transalkylation and disproportionation mechanisms. A catalyst containing the aluminosilicate molecular sieve, ZSM-5, is claimed to exhibit no deactivation, even in the absence of hydrogen.

U.S. Ser. No. 285,105, filed Dec. 15, 1988, now U.S. Pat. No. 4,962,258, teaches that gallium-containing molecular sieve catalyst compositions are effective for liquid phase xylene isomerization as their deactivation rate is less than that of similar catalyst compositions which have been found effective for vapor or gas phase isomerization.

While commercial chemical reactions have not been carried out under supercritical conditions, there has been commercial interest in the use of extraction and separation processes above the critical temperature. This interest is based upon the greatly increased solubility and improved mass transfer rates obtained when solvents are at elevated temperatures and pressures. Much less has been written on the effect of supercritical pressures and temperatures on reactions, particularly heterogeneous, catalyzed reactions.

At pressures above the critical pressure of the reactant mixture, it is possible to isobarically heat or cool the reactor feed and effluent and pass back and forth between the liquid and gas phases without phase separation. This factor would allow the design of a more efficient feed-effluent heat exchanger and allow a reduction in fuel consumption in processes which require a furnace in front of the reactor.

In the case of xylene isomerization, another benefit can be realized if the use of supercritical conditions allows the elimination of hydrogen (or at least its substantial reduction) which is normally a component of the feed to a currently practiced vapor or gas phase xylene isomerization. The reduction or elimination of hydrogen allows size reduction or elimination of the recycle gas compressor which reduces energy consumption. A third advantage to be found in xylene isomerization under supercritical conditions relative to liquid phase processes is the possibility that catalyst activity will be increased at the higher temperatures required to achieve supercriticality and so smaller reactors and smaller catalyst loads would be required compared to liquid phase processes. Opposed to these benefits, the higher pressures required in supercritical operations require that thicker-walled reactors and other equipment such as heat exchangers are needed. Also, the higher temperatures and pressures employed in a catalyzed reaction such as xylene isomerization put more demand on catalyst properties as the usual isomerization catalysts deactivate more rapidly at higher temperature.

Now it has been found that these and other benefits can be obtained by carrying out the xylene isomerization under supercritical conditions employing selected isomerization catalysts and operating in a region of both supercritical temperature and supercritical pressure.

BRIEF DESCRIPTION OF THE INVENTION

Figure 1:
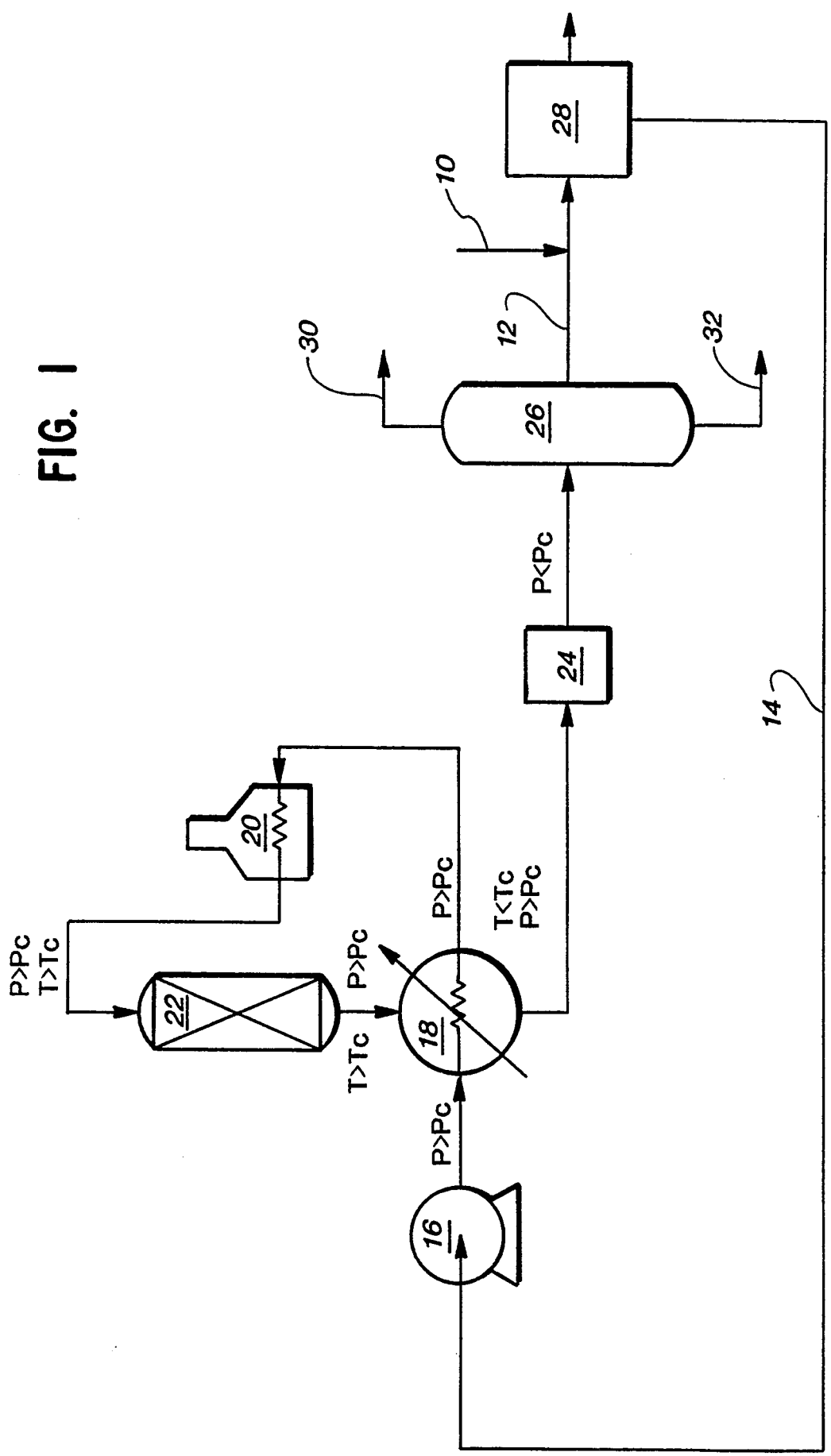
FIG. 1 shows a simplified flow diagram for a supercritical conditions xylene isomerization process.

The invention described herein is a process to catalytically isomerize a stream comprising one or more xylenes and, optionally, a minor amount of ethylbenzene which comprises contacting said stream under supercritical conditions at a temperature and pressure above the critical temperature and pressure of the mixture of components in said stream with a catalyst to form a product rich in p-xylene and thereafter reducing the temperature of said product such that is passes directly from said supercritical conditions to a liquid phase at a pressure above said critical pressure.

In another aspect the invention described herein is a process to catalytically isomerize a stream comprising one or more xylenes and, optionally, a minor amount of ethylbenzene which comprises contacting said stream under supercritical conditions at a temperature and pressure above the critical temperature and pressure of the mixture of components in said stream with an aluminum-, boron-, gallium- or iron-containing, crystalline, silicate molecular sieve catalyst incorporated in a silica, alumina, or silica-alumina matrix to form a product rich in p-xylene and thereafter reducing the temperature of said product such that is passes directly from said supercritical conditions to a liquid phase at a pressure above the critical pressure.

In still another aspect, it describes a precess to catalytically isomerize a stream comprising one or more xylenes and, optionally, a minor amount of ethylbenzene comprising contacting said stream under supercritical conditions at a temperature and pressure above the critical temperature and pressure of the mixture of components in said stream with a catalyst composition which contains about 10 to about 80 weight percent, based upon the total weight of said catalyst composition, of a gallium-containing, crystalline, silicate molecular sieve incorporated into about 20 to about 90 weight percent, based upon the total weight of said catalyst composition, of a silica matrix, said sieve containing about 0.1 to 8 weight percent gallium, calculated as the metal to form a product rich in p-xylene and thereafter reducing the temperature of said product such that it passes directly from said supercritical conditions to product liquid phase at a pressure above the critical pressure.

In yet another aspect, it describes a process to catalytically isomerize a stream comprising one or more xylenes and, optionally, a minor amount of ethylbenzene comprising contacting said stream under supercritical conditions at a temperature and pressure above the critical temperature and pressure of the mixture of components in said stream with a catalyst composition which contains about 10 to about 80 weight percent, based upon the total weight of said catalyst composition, of a gallium-containing, crystalline, silicate molecular sieve incorporated into about 20 to about 90 weight percent, based upon the total weight of said catalyst composition, of a silica matrix, said sieve containing about 0.1 to about 8 weight percent gallium, calculated as the metal, said sieve providing an x-ray pattern comprising the following x-ray diffraction lines and strengths when obtained using copper K alpha radiation:

| Interplanar Spacing Angstroms | Assigned Strength | Interplanar Spacing Angstroms | Assigned Strength |
| --- | --- | --- | --- |
| 11.14 ± 0.5 | S-VS | 3.82 ± 0.1 | M-S |
| 10.05 ± 0.4 | S-VS | 3.75 ± 0.1 | W-M |
| 6.36 ± 0.2 | W | 3.72 ± 0.1 | W-M |
| 5.99 ± 0.15 | W | 3.64 ± 0.1 | W-M |
| 5.57 ± 0.15 | W | 3.34 ± 0.05 | W |
| 3.85 ± 0.1 | S-VS | 2.98 ± 0.04 | W | to form a product rich in p-xylene and thereafter reducing the temperature of said product such that it passes directly from said supercritical conditions to a liquid phase at a pressure above said critical pressure.

DETAILED DESCRIPTION OF THE INVENTION

FIG. 1 a simplified flow diagram for one embodiment of a supercritical conditions xylene isomerization process is shown. Fresh feed, generally containing a near equilibrium distribution of the xylenes, is introduced ahead of the p-xylene separation section through line 10. The fresh feed is mixed with the $C_8$-aromatics-rich effluent from distillation section 26 which passes through line 12. The pX is separated in pX separation section 28 from the combined stream by any one of a number of methods known to those skilled in the art, including crystallization and selective adsorption on a molecular sieve-containing adsorbent. A stream lean in pX from pX separation section 28 is recycled to reactor 22 through line 14. This recycled stream is first passed through pump 16, which pressurizes the isomerization feed above its critical pressure ($P > Pc$) before it enters the cold end of feed-effluent heat exchanger 18. It is desirable to keep the hot and cold isomerization streams in feed-effluent heat exchanger 18 above their critical pressures to avoid the formation of a vapor phase and its associated low heat transfer coefficients. The isomerizer feed temperature is increased above its critical value ($T > Tc$) in furnace 20 so that when the feed enters isomerizer 22, the temperature is greater than Tc and the pressure is greater than Pc. The reactor effluent is cooled at a pressure greater than Pc to a temperature below Tc upon passing through the feed-effluent heat exchanger such that it passes from the gas phase to the liquid phase without a phase change. It is cooled to a temperature useful for subsequent steps in the process.

For a typical xylene-containing feed to the supercritical isomerizer which is about 20 wt. % o-xylene, 45 wt. % m-xylene, 8 wt. % p-xylene, 15 wt. % ethyl benzene, and 12 wt. % other hydrocarbons, the critical pressure is above about 500 psig and the critical temperature is above about 650° F.

It is beneficial to recover energy as the pressure of the cold effluent from heat exchanger 18 is reduced ($P < Pc$) before it enters distillation section 26. For example, energy can be recovered by letting the pressure down through turbine 24. The effluent is finally distilled in distillation section 26 to remove a portion of the light and heavy by-products formed in the isomerization reactor which prevents their buildup in the reactor feed.

In this embodiment, hydrogen is not added to the reactor feed stream. However, it may be beneficial to add a small amount of hydrogen to reduce the rate of catalyst deactivation. If hydrogen is added, it is desirable to add it at a level below its solubility in the isomerization stream at reactor pressure and at temperatures present in the feed-effluent heat exchanger to avoid the formation of a vapor phase and its associated low heat transfer coefficient. This amount of hydrogen is substantially below the amount of hydrogen that is added to the feed during currently practiced gas or vapor phase xylene isomerization, and therefore, the size of the gas compressor needed for a supercritical conditions process is reduced substantially.

Figure 2:
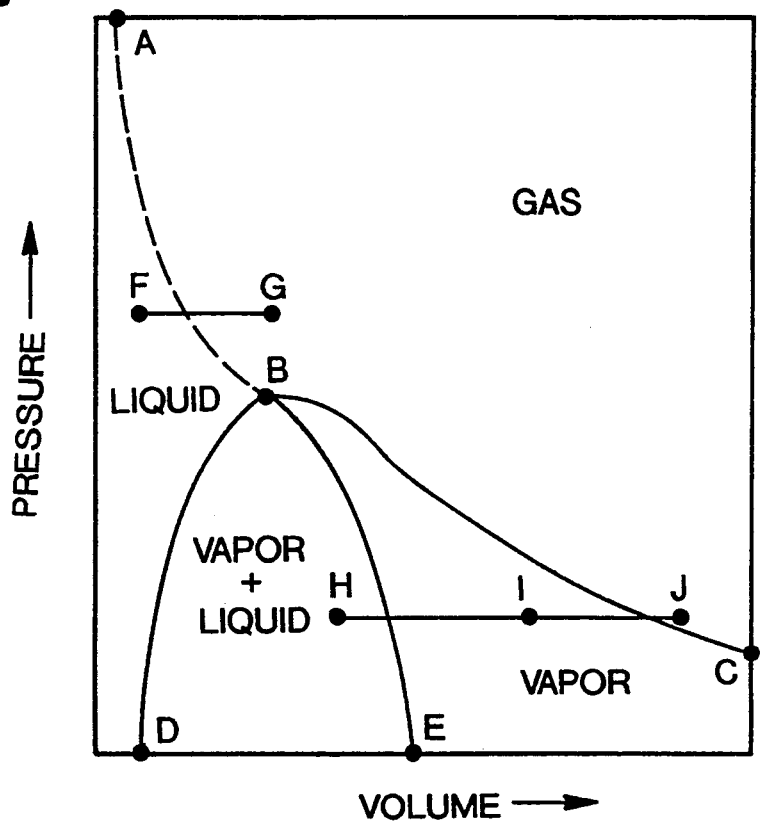
FIG. 2 shows a typical pressure-volume phase diagram in the region of the supercritical temperature.

FIG. 2 is useful in describing a major difference between conventional gas or vapor phase xylene isomerization and supercritical conditions xylene isomerization. In FIG. 2, the point B is the critical point. The curve ABC is the critical temperature isotherm. Points above and to the right of curve ABC represent points in the gas phase. Vapor is distinguished from gas, in that it is not possible to produce condensate by isothermally compressing a gas. The heating of the feed and the cooling of the effluent in the feed-effluent heat exchanger occurs essentially isobarically. Above the critical pressure, there is no physical distinction between the liquid and gas phases. Thus, in a supercritical conditions xylene isomerization process, where the streams inside the feed-effluent heat exchanger are above their critical pressures, it is possible to isobarically cool the reactor effluent such that it passes from the gas phase to the liquid phase without a phase change along a path, such as the curve GF.

Current vapor or gas phase xylene isomerization is conducted at pressures well below the critical pressure, at points on FIG. 2, such as I, which represents vapor phase operation, or J, which represents gas phase operation. Upon cooling the reactor effluent, in the feed-effluent heat exchanger, along a typical path, such as curve JIH, liquid condenses from the vapor phase, and two distinct phases coexist in the heat exchanger.

Figure 3:
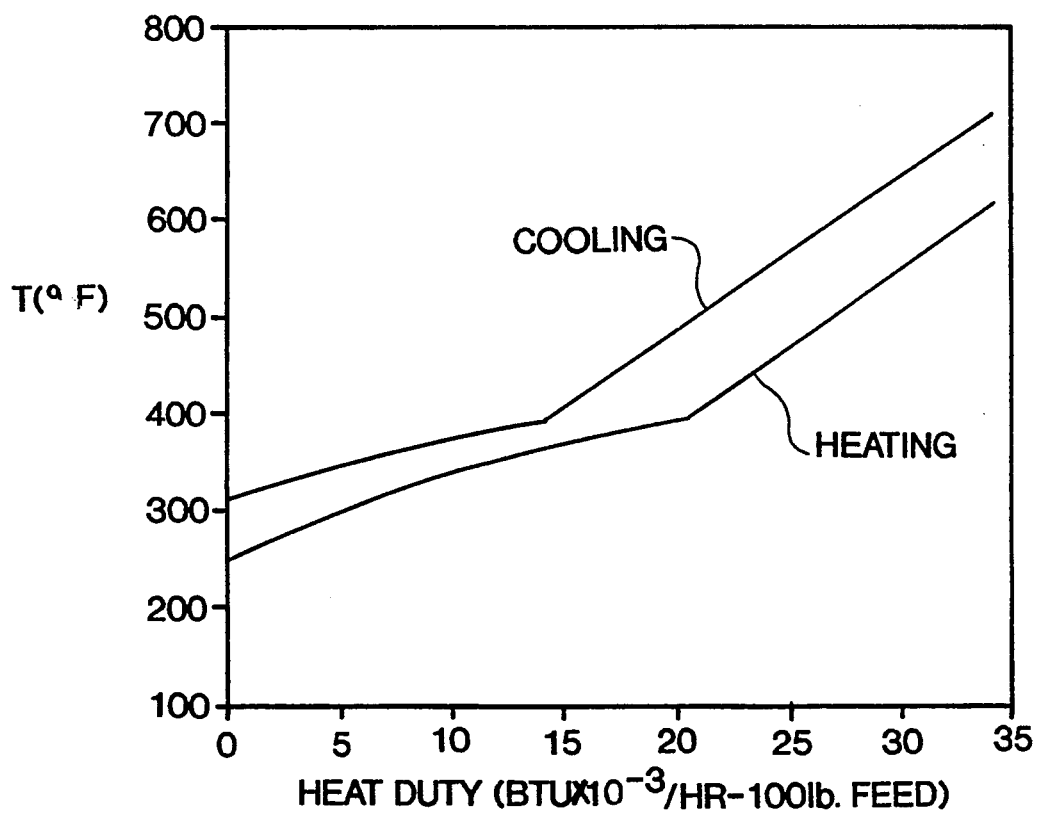
FIG. 3 shows calculated heating and cooling curves for the feed-effluent heat exchanger in a typical gas phase xylene isomerization.
Figure 4:
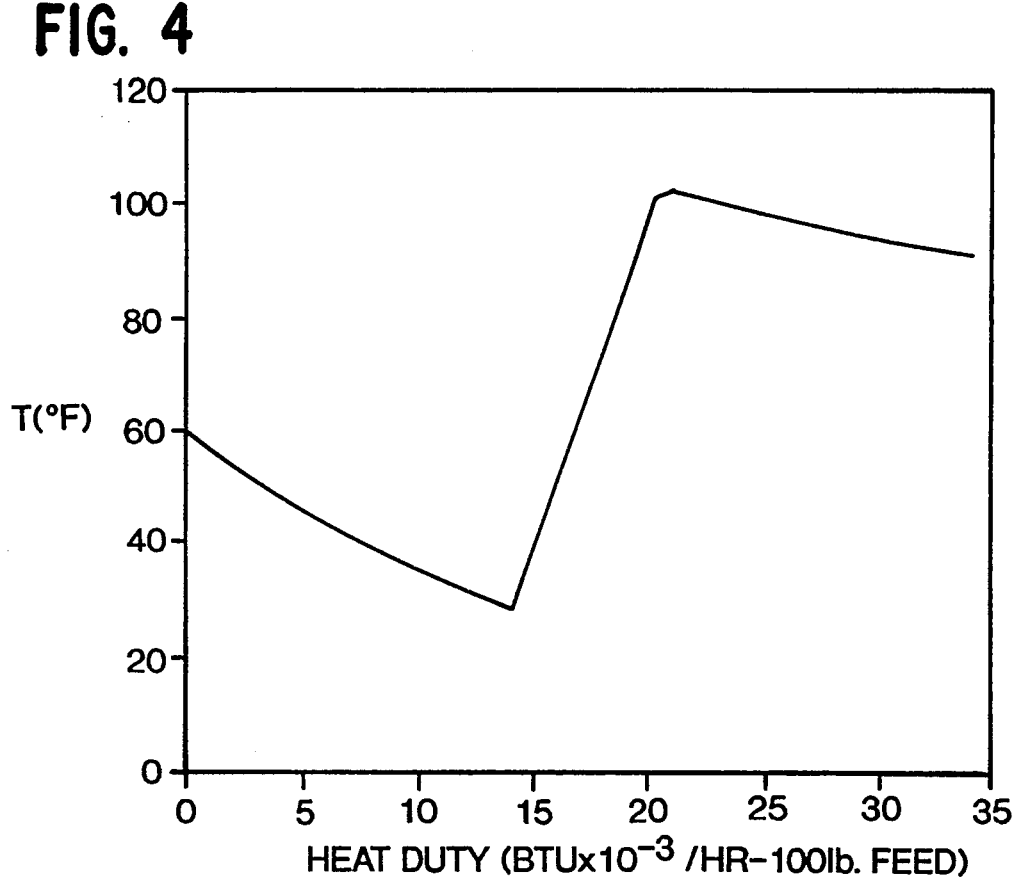
FIG. 4 shows the calculated temperature approach as a function of heat duty for the heating and cooling curves of FIG. 3.
Figure 5:
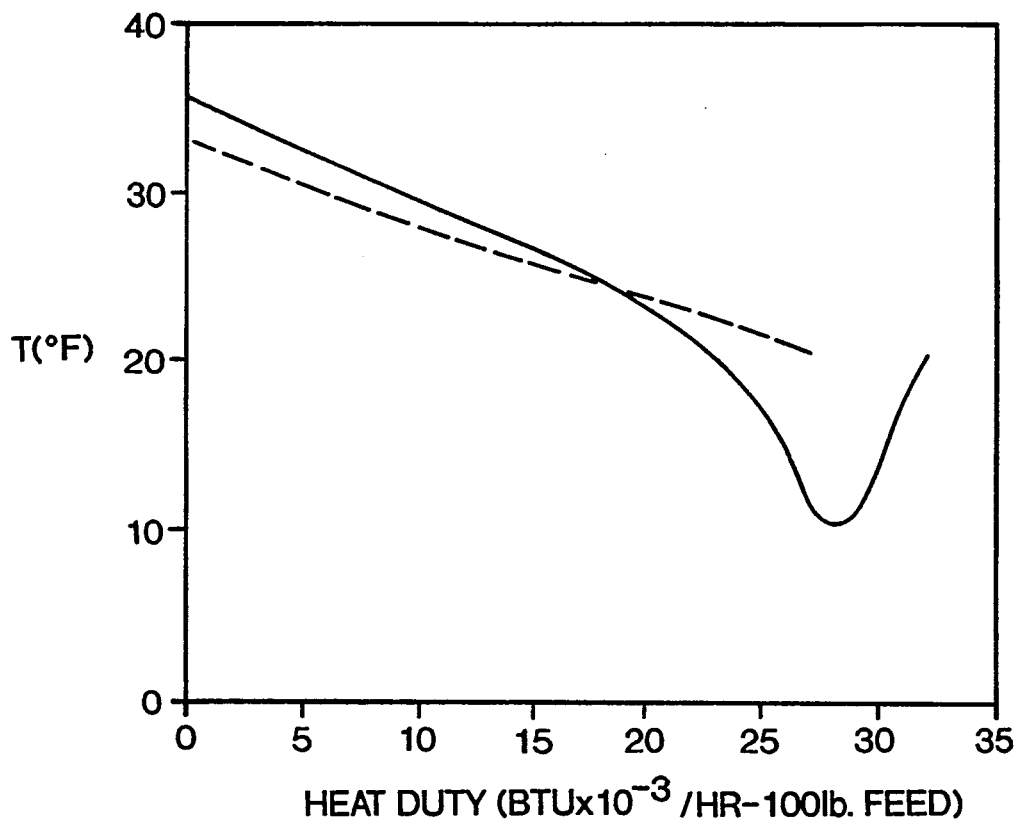
FIG. 5 shows the calculated temperature approach as a function of heat duty for a supercritical conditions xylene isomerization process operating at 614.7 (solid line) and 1000 (dotted line) psia for a 20° F. temperature approach at the hot end of the feed-effluent heat exchanger.

FIGS. 3–5 are useful in describing how an internal temperature pinch point can occur within the feed-effluent heat exchangers of current processes, and how the magnitude of the temperature pinch can be reduced or an internal temperature pinch eliminated for a supercritical conditions process.

FIG. 3 shows calculated heating and cooling curves for a typical gas phase process. These curves and those of FIGS. 4 and 5 were calculated using the Redlich-Kwong-Soave equation of state and the Racket equation for liquid volume calculations. The following reactor feed and effluent compositions were used in the calculation:

| Component | Mass Fraction in Feed | Mass Fraction in Effluent |
| --- | --- | --- |
| Hydrogen | 0.04000 | 0.04000 |
| ethylbenzene | 0.15539 | 0.12130 |
| p-xylene | 0.08475 | 0.16915 |
| m-xylene | 0.44654 | 0.37266 |
| o-xylene | 0.18972 | 0.16394 |
| Other hydrocarbons | 0.08360 | 0.13295 |

This composition gives a hydrogen:hydrocarbon mol ratio of approximately 2. Reactor pressure was assumed to be 200 psia. A temperature approach of 60° F. was specified for the cold end of the feed-effluent heat exchanger, which gives rise to a temperature approach of about 92° F. at the hot end, which is believed typical of current processes.

A sharp break occurs in the heating and cooling curves of present processes at the point where all of the feed has been vaporized, and the effluent starts to condense. This gives rise to an internal temperature pinch point, as shown in FIG. 4. The temperature approach at the pinch point is about 60° F. lower than at the hot end of the feed-effluent heat exchanger. Lower temperature approaches at the hot end are possible for a gas or vapor phase process, but due to low vapor phase heat transfer coefficients, a substantial reduction in approach temperature would require a heat exchanger that would be large and costly. However, for comparison to the supercritical conditions process, another gas phase process simulation was performed, with a specified approach temperature at the cold end of 18° F. This gave rise to a calculated approach temperature at the hot end of about 23° F., and the temperature approach at the pinch point was reduced to about 5° F.

FIG. 5 shows by the solid line temperature approach versus heat duty for a supercritical process operating at 614.7 psia and a temperature of the cold stream at the hot end of the exchanger of 700° F. and a temperature approach of 20° F. Reactor feed and effluent composition was the same as assumed for FIG. 3, except hydrogen was absent. Since hydrogen is absent the hydrocarbon components are normalized to 100%. At 614.7 psia, an internal temperature pinch point is observed. However, for a temperature approach at the hot end of 20° F., the temperature approach at the pinch point is only about 11° F., compared to about 5° F. for a typical current gas phase process for the same hot end temperature approach.

FIG. 5 also shows by the dotted line temperature approach versus heat duty for a supercritical conditions xylene isomerization process operating at 1000 psia for the same feed composition as assumed for FIG. 3, except hydrogen was absent. At 1000 psia the temperature pinch point no longer occurs internally but has moved to the hot end of the exchanger.

At pressures above Pc the magnitude of the temperature pinch becomes smaller and an internal temperature pinch is eventually eliminated as pressure is increased. Thus, to maximize temperature approach (which is proportional to the rate of heat transfer) within the heat exchanger, while minimizing temperature approach at the hot end of the heat exchanger (which minimizes fuel consumption in the furnace), it is desirable to operate at higher pressures. The pressure for a supercritical conditions process must exceed Pc of the isomerization stream. To allow a substantial reduction in the magnitude of the temperature pinch relative to existing vapor or gas processes, a reduced pressure, defined as reactor pressure divided by the critical pressure, of greater than about 1.2 is preferred. It is believed that an internal temperature pinch will not occur for reduced pressures of greater than about 2, and therefore, it is believed that no additional benefits will be gained by operating at reduced pressures above about 2. The benefit of reducing the magnitude of or eliminating an internal temperature pinch upon operating at higher pressures is balanced by the increased cost of equipment needed to withstand the higher pressures.

It is also a requirement of a supercritical conditions process that reactor temperature be above the critical temperature of the isomerization stream. However, it is generally advantageous to minimize reactor temperature, while meeting this requirement, to reduce catalyst deactivation. Other than increased activity, and therefore, reduced catalyst cost, there is little benefit to operating at temperatures substantially higher than the critical temperature.

Catalysts useful for the invention described herein include a solid acid catalyst component, such as, but not limited to, amorphous silica-alumina and aluminum-, boron-, gallium-, or iron-containing crystalline silicate molecular sieve catalyst compositions. Preferred molecular sieves should have framework topology designations of MFI, MEL, FER, TON, EUO, or MTT, as proposed in W. H. Meier, and D. H. Olson, "Atlas of Zeolite Structure Types," Structure Commission of the International Zeolite Association (1978) and A. C. Rohrman, Jr., R. B. LaPierre, J. L. Schlenker, J. D. Wood, E. W. Valyocsik, M. K. Rubin, J. B. Higgins, and W. J. Rohrbaugh, Zeolites, 5, 353 (1985), and/or have framework topologies similar to ZSM-5 (U.S. Pat. No. 3,702,886), ZSM-11 (U.S. Pat. No. 3,709,971), ZSM-22, ZSM-23, ZSM-48, ZSM-50, theta-1, ferrierite, Nu-10, KZ-2, ISI-1, EU-1, EU-2, ZBM-30, EU-11, ISI-4, KZ-1, TPZ-3, and AMS-1B (U.S. Pat. No. 4,268,420). Preferred catalysts contain a gallium-containing, crystalline, silicate molecular sieve made as generally described below.

The gallium silicate crystalline molecular sieves used in this invention are characterized by the representative X-ray pattern listed in Table A below and by the composition formula:

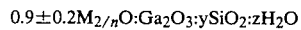

$$0.9 \pm 0.2 M_{2/n}O : Ga_2O_3 : ySiO_2 : zH_2O$$

wherein M is at least one cation, n is the valence of the cation, y is between about 24 and about 600, and z is between 0 and about 160. It is believed that substantially all of the gallium content of the sieves occupies molecular sieve lattice positions or is intimately associated with the molecular sieve crystal lattice, existing in the latter case as individual or small clusters of gallium ions in the sieve pores. Attempts to remove the gallium from the gallium silicate sieves by washing or exchanging with ammonium ion removes little of the gallium and, therefore, the gallium content is believed firmly anchored in the main to the silicate lattice.

TABLE A

| Interplanar Spacing Angstroms | Assigned Strength (1-2) | Interplanar Spacing Angstroms | Assigned Strength (1-2) |
| --- | --- | --- | --- |
| 11.14 ± 0.5 | S-VS | 3.82 ± 0.1 | M-S |
| 10.05 ± 0.4 | S-VS | 3.75 ± 0.1 | W-M |
| 6.36 ± 0.2 | W | 3.72 ± 0.1 | W-M |
| 5.99 ± 0.15 | W | 3.64 ± 0.1 | W-M |

TABLE A-continued

| Interplanar Spacing Angstroms | Assigned Strength (1-2) | Interplanar Spacing Angstroms | Assigned Strength (1-2) |
|---|---|---|---|
| 5.57 ± 0.15 | W | 3.34 ± 0.05 | W |
| 3.85 ± 0.1 | S-VS | 2.98 ± 0.04 | W |

(1) Copper K alpha radiation
(2) VW (<5) = very weak; W (5-20) = weak; M (20-40) = medium; S (40-80) = strong; VS (80-100) = very strong The gallium silicate molecular sieve useful in this invention can be prepared by crystallizing an aqueous mixture, at a controlled pH, of a base, a gallium ion-affording material, an oxide of silicon, and an organic template compound, and, optionally, a gallium mineralizing agent such as 2,4-pentanedione.

Typically, the mol ratios of the various reactants can be varied to product the crystalline gallium silicates of this invention. Specifically, the mol ratios of the initial reactant concentrations are indicated in Table B below:

TABLE B

| | Broad | Preferred | Most Preferred |
|---|---|---|---|
| $SiO_2/Ga_2O_3$ | 24–600 | 24–200 | 32–100 |
| Base/$SiO_2$ | 0.05–5 | 0.05–1 | 0.1–0.5 |
| $H_2O/SiO_2$ | 5–80 | 10–50 | 20–40 |
| Template/$SiO_2$ | 0–1 | 0.01–0.2 | 0.02–0.1 |
| Mineralizer/$Ga_2O_3$ | 0–20 | 0–10 | 0–8 |

By regulation of the quantity of gallium (represented as $Ga_2O_3$ in the reaction mixture, it is possible to vary the $SiO_2/Ga_2O_3$ molar ratio in the final product. In general, it is desirable to have the gallium content of the gallium silicate sieve of this invention between about 0.5 and about 8 percent by weight of gallium. More preferably, the amount of gallium should be between about 1 and about 8 weight percent gallium and, most preferably, between about 2 and about 6.5 weight percent of gallium. Too much gallium in the reaction mixture appears to reduce the sieve crystallinity which reduces the catalytic usefulness of the sieve. Too little gallium makes the sieve ineffective for the purposes of this invention.

More specifically, the material useful in the present invention can be prepared by mixing a base, a gallium ion-affording substance, optionally a gallium mineralizing agent, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing, the final pH is reached by addition of the base, and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.5 and most preferably between about 10.5 and about 12.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the gallium source is a water-soluble gallium compound such as gallium nitrate or gallium acetate or another gallium compound, the anion of which is easily removed during sieve calcination prior to use. Water-insoluble gallium compounds such as the oxide can be used as well. Gallium nitrate is the preferred source of gallium.

Gallium mineralizing agents which are used optionally include ketones, alcohols or organic esters, such as ethanol, butanol, ethylene glycol, methyl ethyl ketone, or 2,4-pentanedione. The latter compound is preferred.

Cations useful in formation of the gallium silicate sieves include the sodium ion and the ammonium ion. The sieves also can be prepared directly in the hydrogen form with an organic base such as ethylenediamine which is removed during calcination. The hydrogen form of the gallium silicate sieve is preferred.

Organic templates useful in preparing the crystalline gallium silicate include alkylammonium cations or precursors thereof such as tetraalkylammonium compounds, especially tetrapropylammonium compounds. A useful organic template is tetra-n-propylammonium bromide. Diamines, such as hexamethylenediamine, can be used.

The crystalline gallium silicate molecular sieve can be prepared by crystallizing a mixture of sources for an oxide of silicon, an oxide of gallium, optionally a mineralizing agent such as 2,4-pentanedione, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 24 to about 600, more preferably from about 24 to about 200 and most preferably from about 32 to about 100. If used, the molar ratio of 2,4-pentanedione to gallium should be below about 20. More preferably, the molar ratio lies between about 0 and about 10 and, most preferably, about 0 and about 8. The molar ratio of base to silicon oxide should be above about 0.05, typically below about 5, preferably between about 0.05 and about 1.0 and most preferably between about 0.1 and about 0.5. The molar ratio of alkylammonium compound, such as tetra-n-propylammonium bromide, to silicon oxide can range from 0 to about 1 or above, typically above about 0.005, preferably between about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 1 to about 25 days, typically is about 1 to about 10 days and preferably is about 1 to about 8 days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 150° C. for about 3 to about 8 days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° C. to about 225° C. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 4 to about 16 hours and is then calcined in air in a manner such that the temperature rise does not exceed 125° C. per hour until a temperature of about 540° C. is reached. Calcination at this temperature usually is continued for about 4 to about 12 hours. The gallium silicate sieves thus made generally have a surface area greater than about 300 sq. meters per gram as measured by the BET procedure.

Alternatively, the gallium-containing crystalline, silicate molecular sieve can be made by treating a crystalline borosilicate or aluminosilicate molecular sieve with a relatively volatile, gallium compound such as gallium chloride in the vapor phase at elevated temperature until active gallium is deposited in the sieve. After cooling, the molecular sieve is washed repeatedly with distilled water to remove chloride and boron or aluminum.

The gallium silicate sieve useful in this invention is admixed with or incorporated within various binders or matrix materials depending upon the intended process use. The crystalline gallium silicates are combined with active or inactive materials, synthetic or naturally occurring zeolites, as well as inorganic or organic materials which would be useful for binding the gallium silicate. Well-known materials include silica, silica-alumina, alumina, magnesia, titania, zirconia, alumina sols, hydrated aluminas, clays such as bentonite or kaolin, or other binders well-known in the art. Typically, the gallium silicate is incorporated within a matrix material by blending with a sol of the matrix material and gelling the resulting mixture or slurrying the sieve with the matrix material and drying. Also, solid particles of the gallium silicate and matrix material can be physically admixed. Typically, such gallium compositions can be pelletized or extruded into useful shapes. The crystalline gallium silicate content can vary anywhere from a few up to 100 weight percent of the total composition. Catalytic compositions can contain about 0.1 weight percent to about 100 weight percent crystalline gallium silicate material and preferably contain about 10 weight percent to about 95 weight percent of such material and most preferably contain about 20 weight percent to about 80 weight percent of such material.

Silica-supported gallium silicate catalyst compositions which are preferred can be made by dry mixing the gallium silicate sieve with a silica source such as Cab-O-Sil manufactured by the Cabot Corp., adding water and stirring. The resulting solid is then dried below about 200° C. and finally calcined between about 350° C. and 700° C.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

General

Catalysts were tested for xylene isomerization at supercritical conditions in a computer controlled pilot plant equipped with a 3 ft by 0.75 in od stainless steel upflow reactor. Five heating zones were used to control temperature in the reactor. The catalyst zone was typically about 1.5 to about 5 in in length, and its center was in the center of the middle zone. The catalyst was sandwiched between glass wool plugs, and 3 mm glass beads were used to fill the rest of the reactor. The space occupied by the glass beads was used as preheat and post heat zones. Temperature was measured by a manual travelling thermocouple placed in a ⅛ in. o.d. thermowell that was centered in the reactor tube. Temperature was recorded every 0.5 in along the length of the catalyst bed, and was typically ±1° F. from the set point. After leaving the reactor, the product flowed through a water jacketed tube to reduce its temperature to about ambient. The product then flowed by gravity into a vapor-liquid separator. Reactor pressure was controlled by maintaining a head pressure on this the separator by flowing nitrogen past the separator and through a control valve. Reactor feed and product were analyzed by capillary gas chromatography .

EXAMPLE 1

A gallium-containing molecular sieve was prepared as follows: 80.68 g of 50% sodium hydroxide solution, 42.03 g gallium nitrate, 50.65 g of acetylacetone, and 60.02 g of tetrapropylammonium bromide were dissolved in 1100.0 g of distilled water. The solution was stirred at room temperature for about 30 min before 350.70 g of Ludox AS-40 silica sol manufactured by E. I. DuPont de Nemours & Co. was added. After stirring for an additional 30 min, the pH was 12.14. This mixture was placed in a stirred Teflon-lined autoclave and heated under autogeneous pressure at 150° C. for 7 days. The solid product was filtered and washed with 8 l of distilled water. It was then dried at 329° F. for 4 hr, ramped linearly to 1000° F. over 4 hr and calcined at 1000° F. for 12 hr.

A 139.49 g portion of the calcined product was added to a solution of 279.54 g of ammonium acetate in 1400 ml of distilled water, and the slurry was stirred over a steam bath for 2 hr. The solids were filtered, washed with 4 l of distilled water, and the wet solids were added to a solution of 280.60 g of ammonium acetate in 1400 ml of distilled water. The slurry was stirred over a steam bath for 2 hr, and then the solids were filtered and washed with 4 l of distilled water. The washed solids were dried at 329° F. for 4 hr, ramped linearly to 950 over 4 hr and calcined at 950° F. for 4 hr.

Analysis of the sieve gave 4.4 wt % Ga and <0.005% Na (by atomic absorption) and 43.3 wt % Si by a wet method.

Powder XRD using copper K alpha radiation gave the following d-spacings and I/I(MAX) values.

| d-spacing (Angstroms) | I/I(MAX) % |
| --- | --- |
| 11.14 | 100 |
| 3.85 | 64 |
| 10.01 | 62 |
| 3.82 | 43 |
| 3.71 | 31 |
| 2.08 | 30 |
| 2.55 | 27 |
| 1.60 | 24 |
| 3.48 | 22 |
| 3.75 | 18 |
| 3.64 | 18 |
| 5.97 | 15 |
| 1.74 | 13 |
| 2.38 | 12 |
| 6.35 | 12 |
| 5.56 | 11 |
| 2.98 | 10 |
| 4.25 | 9 |
| 5.69 | 7 |
| 3.05 | 7 |
| 2.01 | 7 |
| 3.44 | 6 |
| 3.31 | 6 |
| 4.36 | 6 |
| 4.98 | 6 |
| 1.99 | 6 |
| 6.69 | 6 |
| 4.60 | 5 |
| 3.35 | 4 |
| 10.47 | 4 |
| 2.94 | 4 |
| 2.39 | 4 |
| 2.73 | 3 |
| 1.66 | 3 |
| 4.00 | 3 |
| 2.48 | 3 |
| 3.39 | 2 |

EXAMPLE 2

A catalyst composition comprising approximately 60 wt % of a gallium-containing molecular sieve in a silica matrix was prepared by mixing 30.05 g of the calcined ammonium acetate-exchanged product of Example 1 with 20.01 g of Cab-0-Sil HS-5 silica manufactured by the Cabot Corp. and 100 ml of distilled water. This mixture was dried at 329° F. for 4 hr, ramped linearly to 1000° F. over 4 hr, and calcined at 1000° F. for 4 hr. The cooled catalyst composition was crushed and sieved to 18-40 mesh.

EXAMPLE 3

A catalyst composition comprising approximately 60 wt % of a gallium-containing molecular sieve in an alumina matrix was prepared by mixing 30.02 g of the calcined ammonium acetate-exchanged product of Example 1 with 60.69 g of distilled water. A 182.11 g portion of PHF alumina sol from American Cyanamid containing about 11.0 wt % solids was added, and this mixture was blended for about 3 min. A gel was formed by adding 20 ml of concentrated ammonium hydroxide. This gel was dried at 329° F. for 4 hr, ramped linearly to 1000° F. over 4 hr, and calcined at 1000° F. for 12 hr. The cooled catalyst composition was crushed and sieved to 18-40 mesh.

EXAMPLE 4

A ZSM-5-type aluminosilicate molecular sieve was prepared as follows: 20.31 g of a 50% sodium hydroxide solution, 10.03 g of sodium aluminate, and 60.02 g of tetrapropylammonium bromide was dissolved in 701.1 g of distilled water. A 600.2 portion of Ludox AS-40 silica sol manufactured by E. I. DuPont de Nemours & Co. was added to this solution. The pH of this solution was 12.87. The material was heated under autogenous pressure in a stirred autoclave at 160° C. for 3 days. The solid product was filtered and washed with 8 l of distilled water. After air drying, some of the fines were removed by dispersing the solid product in distilled water, letting the large particles settle, and decanting. The solids were filtered and dried at 329° F. for 4 hr, ramped linearly to 1000° F. over 4 hr, and calcined at 1000° F. for 12 hr.

The calcined solids were ammonium acetate-exchanged as follows: 244.47 g of the calcined product was added to a solution of 490.02 g of ammonium acetate in 2500 ml of distilled water, and the slurry was heated over a steam bath for 2 hr. The solids were filtered, washed with 4 l of distilled water, and added to a solution of 490.3 g of ammonium acetate in 2500 ml of distilled water. The slurry was heated over a steam bath for 2 hr, and then the solids were filtered and washed with 4 l of distilled water. The washed solids were dried at 329° F. for 4 hr, ramped linearly to 1000° F. over 4 hr and calcined at 1000° F. for 4 hr.

Powder XRD showed the sieve to be highly crystalline and have the MFI structure. Analysis gave 0.84 wt % Al and 57.2 ppm Na (atomic absorption) and 42.3% Si by a wet technique.

EXAMPLE 5

A catalyst composition comprising approximately 40 wt % of a ZSM-5 aluminosilicate molecular sieve in a silica matrix was prepared by mixing 80.08 g of the calcined ammonium acetate-exchanged product of Example 5 with 120.30 g of Cab-O-Sil S-17 silica from the Cabot Corporation and 375 ml of distilled water. This mixture was dried at 329° F. for 4 hr, ramped linearly to 1000° F. over 4 hr and calcined at 1000° F. for 4 hr. The cooled catalyst composition was crushed and screened to 18-40 mesh.

EXAMPLE 6

A catalyst composition comprising approximately 40 wt % of a ZSM-5 aluminosilicate molecular sieve in an alumina matrix was prepared by mixing 80.01 g of the calcined ammonium acetate exchanged product of Example 5 with 60.45 g of distilled water. A 814.3 g portion of PHF alumina sol from American Cyanamid containing about 11.1 wt % solids was added, and this mixture was blended for about 3 min. A gel was formed by adding 90 ml of concentrated ammonium hydroxide. This gel was dried at 329° F. for 4 hr, ramped linearly to 1000° F. over 4 hr, and calcined at 1000° F. for 12 hr. The cooled catalyst composition was ground and sieved to 18-40 mesh.

EXAMPLE 7

An AMS-1B crystalline borosilicate molecular sieve (hydrogen form) was made according to the teachings of U.S. Pat. No. 4,269,813 and Eur. Appl. 1,587,921. A catalyst composition comprising approximately 40 wt % HAMS-1B in an alumina matrix was made according to the following general procedure. Forty parts of a HAMS-1B crystalline borosilicate molecular sieve was blended with 60 parts Davison VFA alumina. Water was added in an amount that made a good extrusion blend. The moisture content of a good extrusion blend is not too low, so as to cause binding of the extruder, nor too high, so as to produce extrudates of low physical integrity. The extrusion blend was extruded into 1/16 in nominal diameter extrudates. The extrudates were dried at 200° F. for 16 hr. The dried extrudates were calcined in a 4-zone electrically heated rotary calciner. The bed temperatures in the various zones were estimated to be: 600° F., Zone 1; 930°–950° F., Zones 2, 3, and 4. Total residence time in the hot zones was about 1 hr. A deep catalyst bed (greater than 1 in) was used. The calcined extrudates were treated with an ammonium acetate solution comprised of 0.3 g of ammonium acetate and 3.3 g of water per g of catalyst for 1 hr at 100° C. The extrudates were rinsed with deionized water and dried at 400° F. for 16 hr. The once-exchanged extrudates were stage-calcined at 920° F. with a total residence time of about 5 hr. The extrudates were ammonium acetate-exchanged and calcined a second time, as above.

EXAMPLE 8

The catalyst composition comprising approximately 60 wt % of a gallium-containing molecular sieve in a silica matrix of Example 2 was tested for xylene isomerization at supercritical conditions. The feed stream contained approximately 17.3 wt. % ethylbenzene, 8.6 wt % p-xylene, 46.5 wt % m-xylene, 19.8 wt % o-xylene, and 7.8 wt % other hydrocarbons. As shown in Table 1 below, this catalyst exhibited remarkably stable ethylbenzene conversion over a 13 day period, and good percent para-xylene approach to equilibrium (PATE), even though no hydrogen was added with the hydrocarbon feed.

TABLE 1

Xylene Isomerization at Supercritical Conditions Using a Silica-Supported Gallium-Containing Molecular Sieve Catalyst Composition

| Time-on-Stream (days) | Temp. (°F.) | Press. (psig) | WHSV (hr$^{-1}$) | % EB Conv. | % Xylene Loss | PATE |
|---|---|---|---|---|---|---|
| 0.65 | 700 | 600 | 12.03 | 22.95 | 2.34 | 101.16 |
| 1.65 | 700 | 600 | 12.17 | 22.71 | 2.29 | 101.28 |
| 2.65 | 701 | 600 | 12.00 | 22.66 | 2.29 | 101.38 |
| 3.65 | 700 | 600 | 12.17 | 23.04 | 2.28 | 101.53 |
| 4.65 | 700 | 600 | 12.17 | 22.76 | 2.30 | 101.38 |
| 5.65 | 700 | 600 | 12.20 | 22.55 | 2.24 | 101.51 |
| 6.65 | 700 | 600 | 12.18 | 22.40 | 2.22 | 101.49 |
| 7.65 | 700 | 600 | 12.20 | 22.44 | 2.23 | 101.47 |
| 8.65 | 700 | 600 | 12.20 | 22.20 | 2.22 | 101.47 |
| 9.65 | 700 | 600 | 12.01 | 22.30 | 2.22 | 101.40 |
| 10.65 | 700 | 600 | 11.99 | 22.30 | 2.19 | 101.42 |
| 11.65 | 700 | 600 | 12.20 | 22.10 | 2.15 | 101.46 |
| 13.31 | 700 | 600 | 12.17 | 22.33 | 2.11 | 101.99 |

EXAMPLE 9

The catalyst composition comprising approximately 60 wt % of a gallium-containing molecular sieve in an alumina matrix of Example 3 was tested for xylene isomerization at supercritical conditions. The feed contained approximately 16.2 wt % ethylbenezene, 8.8 wt % para-xylene, 46.5 wt % meta-xylene, 19.8 wt % ortho-xylene, and 8.7 wt % other hydrocarbons. No hydrogen was added with the hydrocarbon feed. As shown in Table 2 below, the catalyst of Example 3 was much more active than the catalyst of Example 2, as indicated by comparable % EB conversion at higher weight hourly space velocity (WHSV), but its activity was not as stable.

TABLE 2

Xylene Isomerization at Supercritical Conditions Using an Alumina-Supported, Gallium-Containing Molecular Sieve Catalyst Composition

| Time-on-Stream (days) | Temp. (°F.) | Press. (psig) | WHSV (hr$^{-1}$) | % EB Conv. | % Xylene Loss | PATE |
|---|---|---|---|---|---|---|
| 14.53 | 685 | 600 | 35.60 | 20.50 | 2.34 | 102.03 |
| 15.53 | 685 | 600 | 35.05 | 20.58 | 2.34 | 102.06 |
| 16.53 | 686 | 600 | 35.10 | 20.32 | 2.31 | 102.05 |
| 17.53 | 686 | 600 | 35.55 | 20.13 | 2.28 | 101.95 |
| 18.53 | 685 | 600 | 35.64 | 19.96 | 2.23 | 102.04 |
| 19.53 | 686 | 600 | 35.10 | 19.76 | 2.19 | 101.86 |
| 20.53 | 690 | 600 | 35.10 | 21.83 | 2.50 | 102.55 |
| 21.53 | 690 | 600 | 35.10 | 21.55 | 2.47 | 102.58 |
| 22.53 | 690 | 600 | 35.60 | 21.46 | 2.47 | 102.55 |
| 23.53 | 690 | 600 | 35.15 | 21.35 | 2.43 | 102.65 |
| 24.53 | 690 | 600 | 35.10 | 21.23 | 2.45 | 102.48 |
| 25.53 | 690 | 600 | 35.55 | 20.64 | 2.34 | 102.42 |
| 26.53 | 690 | 600 | 35.15 | 20.80 | 2.35 | 102.50 |

EXAMPLE 10

The catalyst composition comprising approximately 40 wt % of a ZSM-5-type aluminosilicate molecular sieve in a silica matrix of Example 5 was tested for xylene isomerization at supercritical conditions. The hydrocarbon feed had the same composition as in Example 9. No hydrogen was added with the hydrocarbon feed. As shown in Table 3 below, this catalyst deactivated quite rapidly.

TABLE 3

Xylene Isomerization at Supercritical Conditions Using a Silica-Supported ZSM-5 Type Aluminosilicate Molecular Sieve Catalyst Composition

| Time-on-Stream (days) | Temp. (°F.) | Press. (psig) | WHSV (hr$^{-1}$) | % EB Conv. | % Xylene Loss | PATE |
|---|---|---|---|---|---|---|
| 5.69 | 690 | 600 | 9.00 | 17.94 | 1.30 | 97.39 |
| 6.69 | 689 | 600 | 9.00 | 16.83 | 1.21 | 96.88 |
| 7.69 | 698 | 600 | 9.04 | 19.04 | 1.44 | 99.35 |
| 8.69 | 698 | 600 | 9.00 | 18.06 | 1.33 | 99.12 |
| 9.69 | 705 | 600 | 9.14 | 19.84 | 1.46 | 100.15 |
| 10.69 | 705 | 600 | 9.16 | 18.79 | 1.36 | 100.04 |
| 11.69 | 705 | 600 | 9.00 | 18.14 | 1.32 | 99.82 |

EXAMPLE 11

The catalyst composition comprising approximately 40 wt % of a ZSM-5-type aluminosilicate molecular sieve in an alumina matrix of Example 6 was tested for xylene isomerization at supercritical conditions. The hydrocarbon feed had the same composition as in Example 9. No hydrogen was added with the hydrocarbon feed. As shown in Table 4 below, this catalyst also deactivated quite rapidly.

TABLE 4

Xylene Isomerization at Supercritical Conditions Using an Alumina-Supported ZSM-5-Type Aluminosilicate Molecular Sieve Catalyst Composition

| Time-on-Stream (days) | Temp. (°F.) | Press. (psig) | WHSV (hr$^{-1}$) | % EB Conv. | % Xylene Loss | PATE |
|---|---|---|---|---|---|---|
| 6.55 | 691 | 600 | 9.00 | 22.02 | 3.73 | 102.78 |
| 7.55 | 691 | 600 | 9.00 | 21.16 | 3.50 | 102.68 |
| 8.55 | 691 | 600 | 9.00 | 20.36 | 3.31 | 102.41 |
| 9.55 | 691 | 600 | 9.14 | 19.63 | 3.16 | 102.60 |
| 10.55 | 691 | 600 | 8.98 | 19.13 | 3.04 | 102.52 |
| 11.55 | 691 | 600 | 9.00 | 18.79 | 2.96 | 102.40 |

TABLE 4-continued

Xylene Isomerization at Supercritical
Conditions Using an Alumina-Supported
ZSM-5-Type Aluminosilicate Molecular
Sieve Catalyst Composition

| Time-on-Stream (days) | Temp. (°F.) | Press. (psig) | WHSV (hr⁻¹) | % EB Conv. | % Xylene Loss | PATE |
|---|---|---|---|---|---|---|
| 12.55 | 691 | 600 | 9.00 | 18.34 | 2.86 | 102.57 |

EXAMPLE 12

The catalyst composition comprising approximately 40 wt % of an AMS-1B (hydrogen form) borosilicate molecular sieve in an alumina matrix of Example 7 was tested for xylene isomerization at supercritical conditions. The hydrocarbon feed had the same composition as in Example 9. No hydrogen was added with the hydrocarbon feed. As shown in Table 5 below, this catalyst also deactivated quite rapidly.

TABLE 5

Xylene Isomerization at Supercritical
Conditions Using an Alumina-Supported
AMS-1B Borosilicate Molecular Sieve
Catalyst Composition

| Time-on-Stream (days) | Temp. (°F.) | Press. (psig) | WHSV (hr⁻¹) | % EB Conv. | % Xylene Loss | PATE |
|---|---|---|---|---|---|---|
| 8.54 | 686 | 600 | 25.40 | 19.95 | 2.61 | 101.15 |
| 9.54 | 686 | 600 | 25.37 | 18.97 | 2.44 | 100.98 |
| 10.54 | 685 | 600 | 25.37 | 18.57 | 2.37 | 100.77 |
| 11.54 | 685 | 600 | 24.97 | 17.94 | 2.26 | 100.57 |
| 12.54 | 685 | 600 | 25.00 | 17.06 | 2.11 | 100.40 |
| 13.54 | 685 | 600 | 25.33 | 16.60 | 2.04 | 100.28 |
| 14.54 | 685 | 600 | 25.37 | 16.30 | 1.98 | 100.16 |

EXAMPLE 13

A sample of reactor effluent gathered after 5.65 days-on-stream during the catalyst testing for supercritical conditions xylene isomerization described in Example 8 was analyzed and found to contain about 13.4 wt % ethylbenzene, 17.4 wt % p-xylene, 38.8 wt % m-xylene, 17.0 wt % o-xylene, 2.3 wt % benzene, 1.5 wt % toluene, and 9.6 wt % other hydrocarbons. The reactor effluent is a gas, having a pressure above its critical pressure when it is in contact with a gallium-containing molecular sieve catalyst composition at the reactor conditions of 700° F. and 600 psig. In this hypothetical example, the temperature of this stream is reduced to about 287° F. in passing through a feed-effluent heat exchanger, while maintaining the pressure of this stream above 599 psig, such that said stream passes from the gas phase to the liquid phase without a phase change.

What is claimed is:

1. A process to catalytically isomerize a stream comprising one or more xylenes and, optionally, a minor amount of ethylbenzene under supercritical conditions at a temperature and pressure above the critical temperature and pressure of the mixture of components in said stream with a catalyst to form a product rich in p-xylene and thereafter reducing the temperature of said product such that it passes directly from said supercritical conditions to a liquid phase at a pressure above said critical pressure.

2. A process to catalytically isomerize a stream comprising one or more xylenes and, optionally, a minor amount of ethylbenzene which comprises contacting said stream under supercritical conditions at a temperature and pressure above the critical temperature and pressure of the mixture of components in said stream with a catalyst composition comprising an aluminum-, boron-, gallium- or iron-containing, crystalline, silicate molecular sieve incorporated in a silica alumina, or silica-alumina matrix to form a product rich in p-xylene and thereafter reducing the temperature of said product such that it passes directly from said supercritical conditions to a liquid phase at a pressure above said critical pressure.

3. A process to catalytically isomerize a stream comprising one or more xylenes and, optionally, a minor amount of ethylbenzene comprising contacting said stream under supercritical conditions at a temperature and pressure above the critical temperature and pressure of the mixture of components in said stream with a catalyst composition which contains about 10 to about 80 wt %, based upon the total weight of said catalyst composition, of a gallium-containing, crystalline, silicate molecular sieve incorporated into about 20 to about 90 wt %, based upon the total weight of said catalyst composition, of a silica matrix, said sieve containing about 0.1 to about 8 wt % gallium, calculated as the metal, to form a product rich in p-xylene and thereafter reducing the temperature of said product such that is passes directly from said supercritical conditions to a liquid phase at a pressure above said critical pressure.

4. The process of claim 3 wherein the amount of ethylbenzene present in said stream is between about 5 and about 35 wt % of said stream.

5. The process of claim 4 wherein said stream contains an amount of hydrogen up to its level of solubility in said stream at reactor pressure and at a temperature between about 200° and 600° F.

6. The process of claim 1 wherein said critical temperature is above about 650° F. and said critical pressure is above about 500 psig.

7. The process of claim 2 wherein said critical temperature is above about 650° F. and said critical pressure is above about 500 psig.

8. The process of claim 3 wherein said critical temperature is above about 650° F. and said critical pressure is above about 500 psig.

* * * * *